United States Patent [19]

Prober et al.

[11] 4,259,573

[45] Mar. 31, 1981

[54] METHOD OF DETERMINING SMALL CONCENTRATIONS OF CHEMICAL COMPOUNDS BY PLASMA CHROMATOGRAPHY

[75] Inventors: James M. Prober; Rudy J. Dam, both of Wilmington, Del.

[73] Assignee: E. I. Du Pont de Nemours and Company, Wilmington, Del.

[21] Appl. No.: 90,914

[22] Filed: Nov. 5, 1979

[51] Int. Cl.³ .............................................. B01D 59/44
[52] U.S. Cl. .................................. 250/287; 250/282; 250/283
[58] Field of Search ............... 250/287, 281, 282, 283, 250/288

[56] References Cited

U.S. PATENT DOCUMENTS

| 3,621,239 | 11/1971 | Cohen | 250/287 |
| 3,626,180 | 12/1971 | Carroll et al. | 250/287 |
| 3,626,182 | 12/1971 | Cohen | 250/287 |

OTHER PUBLICATIONS

"Instrumental Methods of Analysis", Willard et al., monogram published by D. Von Nostrand Co., 4th Ed., pp. 342-344 and 695.

Primary Examiner—Bruce C. Anderson

[57] ABSTRACT

An accurate method of determining by plasma chromatography the concentration of an ionizable gaseous o volatile chemical species A in air or another gaseous medium. Small, known increments of species A plus, optionally, another calibrant species are introduced in turn into the plasma chromatograph together with the unknown sample; and the respective changes of the amplitude or area of a characteristic ion peak of species A in the unknown sample are measured. The second, optical calibrant, which is different from species A, must have similar kinetic characteristics but a different ion mobility from the ion formed by A. By means of this technique, inaccurate readings caused by background concentration variations are significantly reduced.

8 Claims, 6 Drawing Figures

METHOD OF DETERMINING SMALL CONCENTRATIONS OF CHEMICAL COMPOUNDS BY PLASMA CHROMATOGRAPHY

BACKGROUND OF THE INVENTION

This invention relates to an improved method of determining small concentrations of chemical compounds by means of plasma chromatography and to an apparatus suitable for practicing the method of this invention.

Because of the ever growing concern with environmental problems, it is frequently necessary to monitor low concentrations of pollutants in ambient air or in industrial process gases such as, for example, smoke stack effluents and reactor vents. Government regulations set maximum permissible concentrations of many pollutants, sometimes in terms of parts per billion (ppb).

Plasma Chromatography is particularly well suited for the determination of minute amounts of various chemical species, even in the ppb range. Most fundamental work in the field of plasma chromatography has been done by Franklin GNO Corporation, West Palm Beach, Florida. U.S. Pat. Nos. 3,812,355 to Wernlund et al., 3,845,301 to Wernlund et al., and 3,621,239 to Cohen are representative of the prior art. In a plasma chromatograph, a gas stream carrying one or more chemical substances (gases or vapors) is exposed to an ionization source such as, for example, a radioactive material. Ionizable molecules in the gas stream form ions, which are allowed to drift through the so-called "drift tube" of a plasma chromatograph between a charged shutter grid and a collector at the other end of the drift tube. Various ions present in the drift tube at any time separate according to the ion mobilities, which in turn depend, among others, on the ion mass, size, and shape. The amplitude of the ion current for any given drift time does not necessarily vary in direct proportion to the molecular concentration because there is competition for charge among all species present in the sample gas; so that the ion current amplitude for a given ionic species X may vary, even if the concentration of X is constant, because it is affected by the concentrations of other ionized species in the gas stream, which may not be constant. In order to improve the accuracy of measuring by plasma chromatography low concentrations of a chemical substance in a gas sample with reasonable accuracy, it is necessary to account for variations in concentrations of background species.

SUMMARY OF THE INVENTION

According to the present invention, there is provided an improvement in the method of determining the concentration, $C_A$, of an ionizable species A in a gas sample by plasma chromatography by:

(a) introducing into the plasma chromatograph a gas sample containing an unknown concentration of species A, and determining the size, $A^*$ (amplitude or area), of the characteristic peak of an ion formed by species A in the plasma chromatograph at its characteristic point $k_A$ on a plasmagram correlating ion mobility or drift time with ion current intensity;

(b) while maintaining the flow of the gas sample into the plasma chromatograph, introducing into the plasma chromatograph an inert carrier gas containing a discrete amount $\Delta C_A$ of species A, such that the concentration of species A in the plasma chromatograph is increased by the amount $\Delta \hat{C}_A$, and determining the resulting logarithmic change, $\Delta \ln A^*]_A$, in the size of the characteristic ion peak of species A at point $k_A$ in the plasmagram;

(c) while maintaining the flow of the gas sample into the plasma chromatograph, but cutting off the flow of carrier gas containing species A, introducing into the plasma chromatograph an inert carrier gas containing a discrete amount $\Delta C_B$ of species B having kinetic characteristics similar to those of species A but forming an ion whose mobility is different from that of the ion formed by A, the change in concentration of species B in the plasma chromatograph being $\Delta \hat{C}_B$, and determining the resulting logarithmic change of the size (amplitude or area) $\Delta \ln A^*]_B$ of the characteristic ion peak of species A at point $k_A$ in the plasmagram;

purging the plasma chromatograph with the carrier gas before one or more of the above steps (a) through (c) and maintaining during the entire operation through step (c) known flows of the gas sample and of the carrier gas, either alone or containing either species A or species B;

(d) calculating the concentration $\hat{C}_A$ of species A in the plasma chromatograph from the following equation (1):

$$1/\hat{C}_A = K_0 + K_1\{\Delta \ln A^*]_A\} + K_2\{\Delta \ln A^*]_B\} \quad (1)$$

wherein $A^*$ is the size of the plasmagram peak of the characteristic ion formed by A; $\Delta \ln A^*]_A$ denotes the change in $\ln A^*$ on addition of $\Delta C_A$; $\Delta \ln A^*]_B$ denotes the change in $\ln A^*$ on addition of $\Delta C_B$; and $K_0$, $K_1$, and $K_2$ are calibration constants; and (e) calculating the concentration, $C_A$, of species A in the gas sample by means of the following equation (2)

$$C_A = G \cdot \hat{C}_A \quad (2)$$

wherein G is the ratio of the total gas flow through the plasma chromatograph in step (a), above, to the flow of the gas sample through the sample introduction means;

with the proviso that when the concentrations $C_A$ and $(\hat{C}_A + \Delta C_A)$ are sufficiently smaller than the sum $$\sum_i \hat{C}_i$$

of all other ionizable species concentrations in the plasma chromatograph, so that $\Delta \ln A^*]_A$ is proportional to $\Delta \hat{C}_A$, the above step (c) can be omitted, and the concentration $\hat{C}_A$ of species A in the plasma chromatograph can be calculated from the following equation (3)

$$1/\hat{C}_A = K_0 + K_1\{\Delta \ln A^*]_A\} \quad (3)$$

wherein $K_0$ and $K_1$ have the same meaning as in the above equation (1).

THE DRAWINGS

Figure 4:
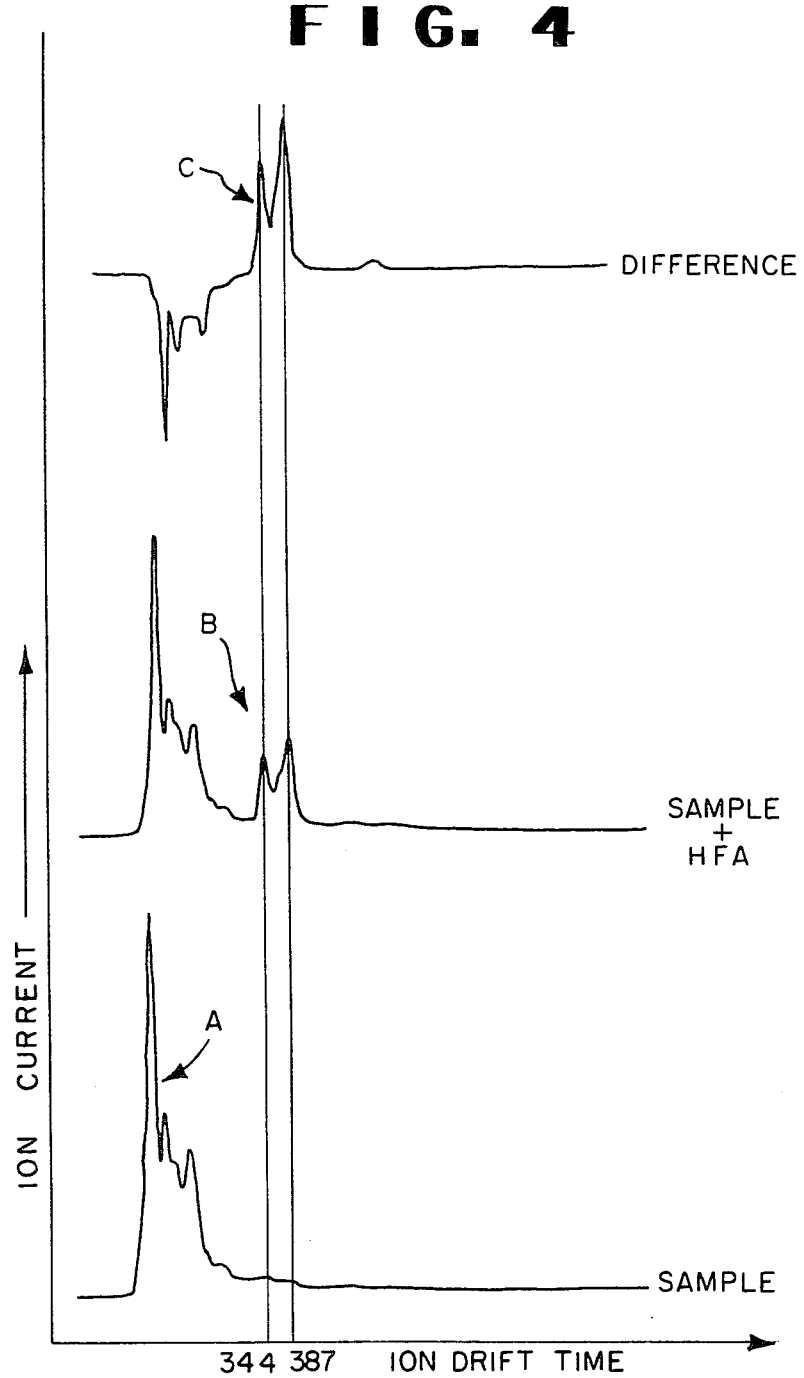

FIG. 4, curves A, B, and C, are plasmagrams, respectively, of an air sample, air sample plus calibrant, and the difference curve.

Figure 5:
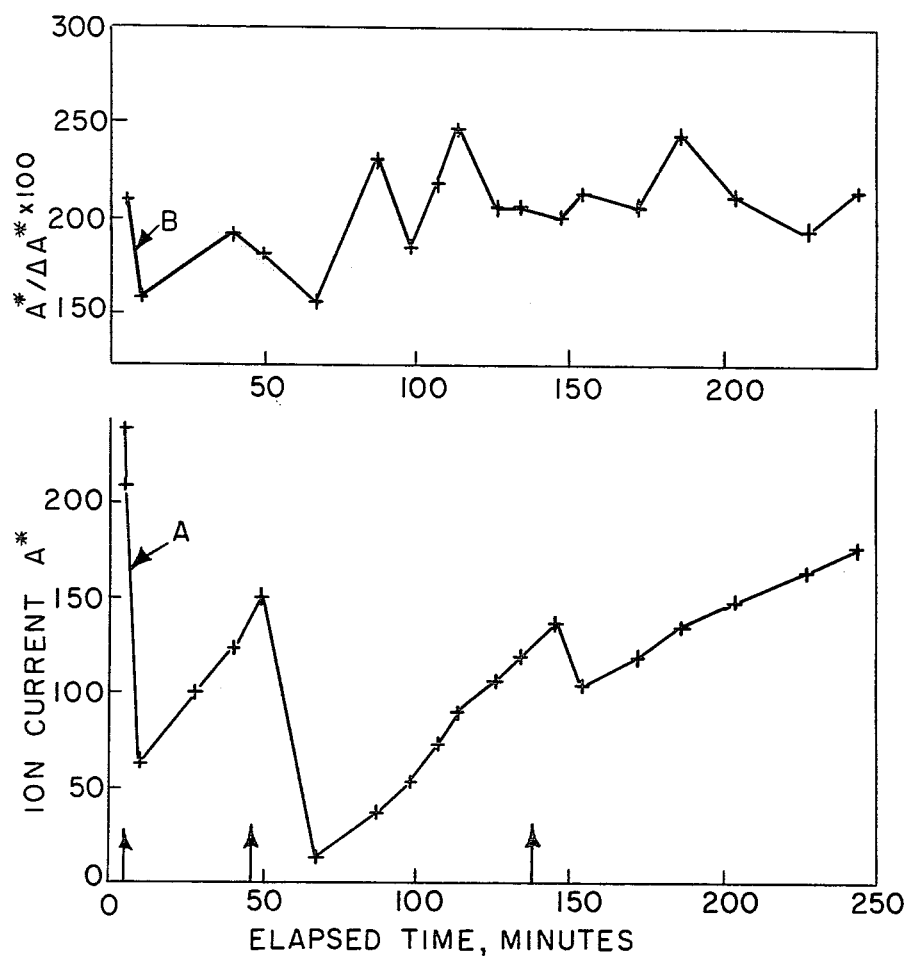

FIG. 5 shows in curve A the variations of the peak height of dimethylnitrosamine in air with changing background conditions. In curve B, the variations of $A^*/\Delta A^*$ are shown.

DETAILED DESCRIPTION OF THE INVENTION

It will be practical, before proceeding further, to list the principal symbols which are used throughout the description and the claims:

A—ionizable chemical species whose concentration is to be determined;
B—ionizable chemical species used as a calibrant;
$C_A, C_B \ldots C_i$—concentrations (vol./vol.) of species A, B ... i in the unknown sample being analyzed;
$\hat{C}_A, \hat{C}_B \ldots \hat{C}_i$—concentrations (vol./vol.) of species A, B ... i in the plasma chromatograph;
$\Delta\hat{C}_A, \Delta\hat{C}_B \ldots \Delta\hat{C}_i$—changes in concentrations (vol./vol.) of species A, B ... i in the plasma chromatograph;
$A^*$—peak size (amplitude or area) of a characteristic ion corresponding to species A on a plasmagram correlating ion mobility or drift time with ion current intensity;
$A^*_c$—peak size of species A corrected for effects of baseline and/or neighboring peaks;
$\Delta A^*$—change in peak size of species A;
$\Delta A^*_c$—change in corrected peak size of species A;
$(\Delta A^*)_A$—change in peak size of species A on addition of species A;
$(\Delta A^*)_B$—change in peak size of species A on addition of species B;
$\Delta \ln A^*]_A$—change of $\ln A^*$ on addition of species A;
$\Delta \ln A^*]_B$—change of $\ln A^*$ on addition of species B;
$C'_A, C'_B \ldots C'_i$—concentrations of species A, B, ... i in a gas stream leaving a known concentration source such as an exponential dilution flask.

The basic equation (1), above, can be derived from a more general equation (4)

$$A^* = \hat{C}_A f(\hat{C}_A, \hat{C}_B \ldots \hat{C}_i), \qquad (4)$$

where f is a function of the concentrations of all species in the plasma chromatograph, including A, which describes their interactions and the resulting response to A; $\hat{C}_A$ and $\hat{C}_B$ are the respective concentrations of substances A and B; and $\hat{C}_i$ are concentrations of all the other ion-forming chemical substances in the plasma chromatograph.

Taking the natural logarithm of equation (4) and then the partial derivatives, first with respect to $\hat{C}_A$ and then with respect to $\hat{C}_B$, one obtains $$\ln A^* = \ln \hat{C}_A + \ln f(\hat{C}_A, \hat{C}_B \ldots \hat{C}_i) \qquad (5)$$

$$\frac{\delta \ln A^*}{\delta \hat{C}_A} = \frac{1}{\hat{C}_A} + \frac{\delta \ln f}{\delta \hat{C}_A} \qquad (6)$$

$$\frac{\delta \ln A^*}{\delta \hat{C}_B} = \frac{\delta \ln f}{\delta \hat{C}_B} \qquad (7)$$

If species B obeys ion-molecule reaction kinetics in a manner similar to species A, the partial derivatives $$\frac{\delta \ln f}{\delta \hat{C}_A} \text{ and } \frac{\delta \ln f}{\delta \hat{C}_B}$$

will differ only by a constant factor, so that $$\frac{\delta \ln f}{\delta \hat{C}_A} = K \frac{\delta \ln f}{\delta \hat{C}_B} \qquad (8)$$

where K is related to the respective rate constants for ionization of species A and B in the ion-molecule reaction region of the plasma chromatograph. Combining equations (6), (7), and (8) gives $$\frac{1}{\hat{C}_A} = \frac{\delta \ln A^*}{\delta \hat{C}_A} - K \frac{\delta \ln A^*}{\delta \hat{C}_B} \qquad (9)$$

For small but finite changes $\Delta \hat{C}_A$ and $\hat{C}_B$ in the concentrations of A and B in the plasma chromatograph, equation (9) can be replaced by equation (10), as follows:

$$\frac{1}{\hat{C}_A} = \frac{\Delta \ln A^*]_A}{\Delta \hat{C}_A} - K \frac{\Delta \ln A^*]_B}{\Delta \hat{C}_B} \qquad (10)$$

This equation relates the concentration of species A, $\hat{C}_A$, to measurable changes in spectral amplitude or area resulting from known additions $\Delta \hat{C}_A$ and $\Delta \hat{C}_B$ to the plasma chromatograph. Since $\Delta \hat{C}_A$ and $\Delta \hat{C}_B$ are for all practical purposes constant, one can convert the above equation (10) into the form given in equation (1), above, wherein the additive constant, $K_0$, is a correction factor which is used to account for any error due to the use of difference values instead of differential expressions. The calibration constants $K_0$, $K_1$, and $K_2$ can be readily determined by regression analysis, as shall be explained later in this disclosure.

When $\hat{C}_A$ is small compared to the sum of all other ionizable species concentrations, $$\sum_i \hat{C}_i,$$

the response of the plasma chromatograph to $\Delta \hat{C}_A$ additions frequently is linear, and the last term of equation (1), which introduces a linearity correction, can be ignored. In such case it is not necessary to additionally introduce into the plasma chromatograph calibrant B; it is sufficient to calibrate the instrument with substance A alone. The equation will then be simplified to the above equation (3). It has to be borne in mind that in plasma chromatography, where all components interact with one another and compete for electrical charge, the change of concentration of any of those components or introduction of another component affects the ionizability of all the other components. Therefore, the linear relationship reflected by equation (3) is valid when the concentration of species A is small relative to the sum of the concentrations of the other ion-forming species.

Figure 1:
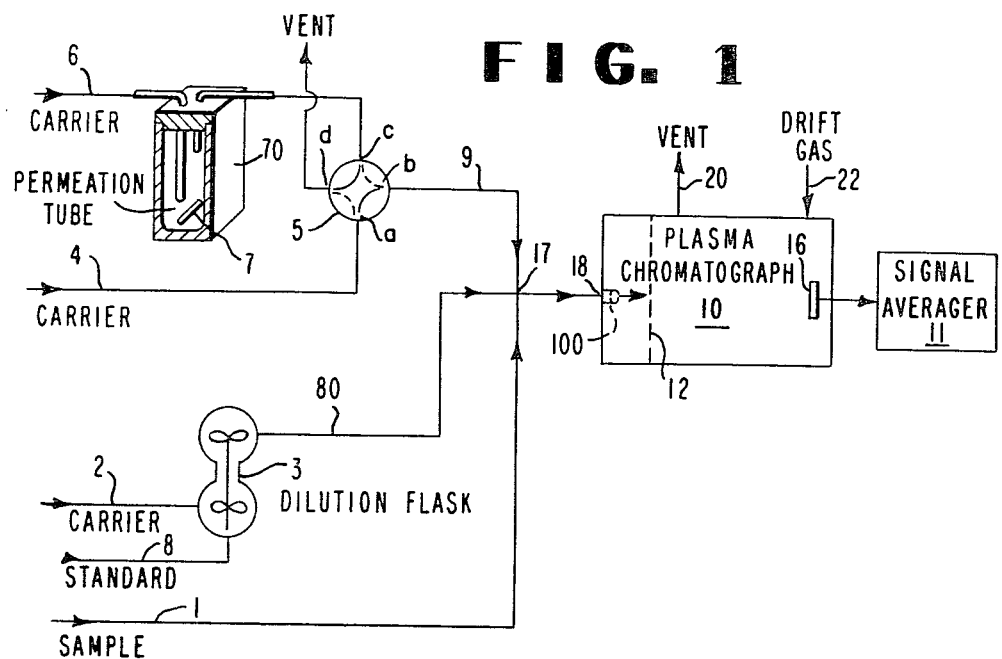
FIG. 1 is a schematic drawing of the basic components of a calibration system for the plasma chromatograph.

In order to carry out measurements according to the method of this invention, it is necessary to have a sampling system suitable for introducing into the plasma chromatograph gas samples and calibrants, means for accurately determining calibrant concentrations, and means for displaying, storing, and/or recording spectral data. It is practical to use specialized electronic equipment capable of time averaging, storing, and recalling plasmagrams or equivalent spectral data. The basic plasma chromatograph can be obtained from PCP, Inc. in West Palm Beach, Florida. In its simplest form, a plasma chromatograph is a drift tube containing an ionization source, a shutter grid, and a collector. It can be combined with associated equipment according to the present invention, for example, as shown in FIG. 1.

Line 1 conveys the sample gas to be analyzed to the first inlet port of a four-port junction connector 17, which can receive three gas streams for input into the gas inlet port 18 of the plasma chromatograph 10. Gases entering the plasma chromatograph pass by or through the ion source 100. Line 2 introduces an inert carrier gas, typically nitrogen, into an exponential dilution flask 3, which is used to furnish a known concentration $C'_A$ of molecule of interest (A) to the inlet port 18. This is accomplished by injecting a known concentration $C'_A(o)$ of standard gas A into the flask inlet 8 at an initial time $t_o$. As nitrogen purges the dilution flask, the concentration $C'_A(t)$ of gas A supplied to the connector 17 through line 80 varies exponentially with time according to the following equation (11):

$$C'_A(t) = C'_A(o)e^{-\alpha t} \quad (11)$$

where $\alpha$ is the ratio (nitrogen flow rate, cc/min): (flask volume, cc), and t is elapsed time in minutes.

Thus, a continuously varying but known concentration of A can be supplied to the plasma chromatograph 10. Dilution flask techniques are well known to the art. See, for example, J. J. Ritter and N. K. Adams, Anal. Chem 48, 612 (1976). Other systems, such as regulated gas cylinder containing species A diluted with nitrogen, could be used but are not considered as practical as the exponential dilution flask, which can deliver A to the plasma chromatograph at a concentration which varies continuously over a wide range. Dynamic standards such as the exponential dilution flask also are inherently more accurate and reliable than static standards at very low concentrations.

A regulated flow of carrier gas, such as nitrogen, is supplied through line 4 to the first of two ports of four-way valve 5, having two inlet ports, a and c, and two outlet ports, b and d. Calibrant source 7 delivers a constant concentration, $C'_A$, of species A to the second inlet port, c, of valve 5. A portion of the calibrant source output may be vented to exhaust (not shown), while the remainder is remixed with pure carrier gas to provide an adjustable concentration of A to valve 5. The specific calibrant source illustrated in FIG. 1 is a permeation tube, which is housed in a thermostatted container, 70. Permeation devices are well known and are generally accepted for providing stable, accurate gas standards, for example, for use in calibrating ambient air monitors. A discussion of permeation devices by F. F. Scaringelli, et al. can be found in Anal. Chem. 42, 871 (1970).

The first of two outlet ports of valve 5 is connected to a vent, while the second outlet port communicates with the four-port connector 17. In the position shown in FIG. 1 in solid lines, valve 5 vents the calibrant in carrier gas stream from line 6 and passes the pure carrier gas stream from line 4 through line 9 to connector 17. In the position shown by broken lines, carrier gas is vented, while the calibrant stream is admitted to connector 17. In this way, a continuous stream of either carrier gas alone or carrier gas containing calibrant A flows through connector 17 to plasma chromatograph 10. This continuous stream is maintained at constant flow conditions by means of sufficient vacuum at the plasma chromatograph's vent 20, as well as of control valves and regulators (not shown) on lines 4 and 6.

Figure 2:
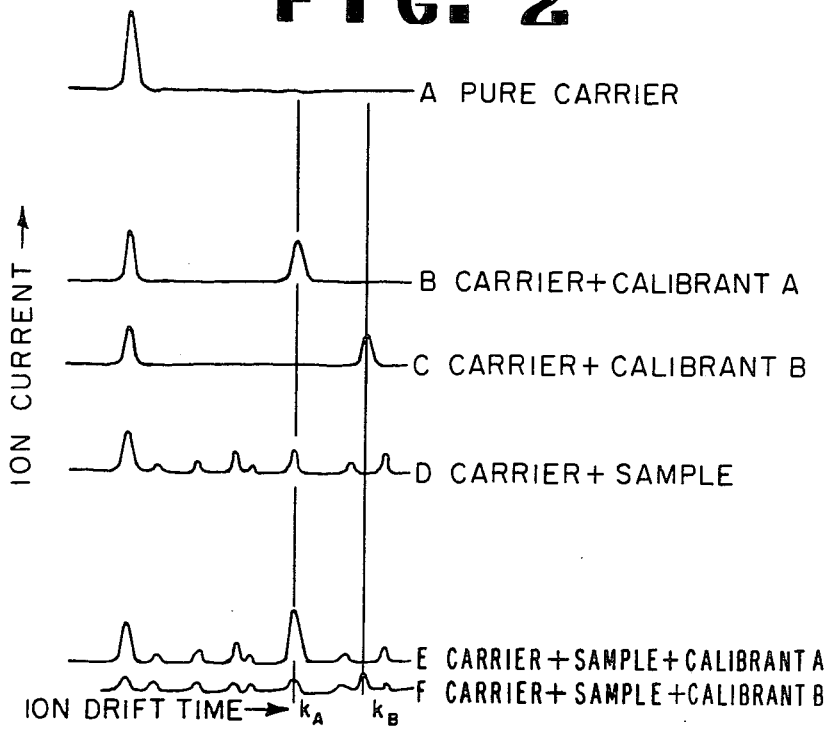
FIG. 2 represents typical plasmagrams produced by a signal averager.

A signal averager 11, such as, for example, Nicolet 1170 (Nicolet Instrument Company), is connected to the collector (output electrode) 16 of the plasma chromatograph via a preamplifier, not shown. It time-averages, records, and displays plasmagrams of the mixture of ion species which reach the collector between pulsations of grid 12. FIG. 2 shows typical ten second time-averaged waveform plasmagrams (ionic current versus drift time) produced by the signal averager. One can use, in addition, a strip chart recorder, which is operated in conjunction with an instrument such as, for example, a PAR CW-1 boxcar integrator of Princeton Applied Research Corporation, to keep a running record of changes in ion current amplitude at any given ionic mobility in the plasmagram as a function of elapsed time (such as shown, for example, in FIG. 5). One should always keep in mind that amplitude changes corresponding to a given species do not necessarily reflect changes in that species' concentration.

Calibration Method

First, the concentration of the calibrant species A in the gas stream flowing from the calibrant source 7 into the four-way valve 5 and thence through line 9 into the plasma chromatograph must be determined. Valve 5 is set as shown in FIG. 1 to admit to the plasma chromatograph 10 carrier gas from line 4, while venting the calibrant from line 6. Carrier gas from line 2 circulates through the exponential dilution flask 3 and thence to the four-port connector 17. Simultaneously, carrier gas also enters the four-port connector 17 through line 1. In neither case does the carrier gas carry the species of interest A, whether in a known or an unknown concentration. Initially, then, the plasma chromatograph will be purged of background impurities and the plasmagram cleared of the corresponding noise signals at the selected drift time characteristic of the species of interest A (point $k_A$ on the graphs of FIG. 2), while the volume flow condition at port 18 is measured. It is practical to maintain this volume flow constant, but this is not a requirement. When the plasmagram appears clear at the selected point $k_A$ (curve A in FIG. 2), valve 5 is turned to the dotted position to admit the calibrant gas from permeation tube 7 into the plasma chromatograph. After the plasmagram of this species is obtained (curve B in FIG. 2), valve 5 is returned to its original position, so that the carrier gas again enters connector 17 through line 4 while it also continues to circulate through both the exponential dilution flask 3 and sample line 1 into the plasma chromatograph. When the background plasmagram is again clear, a standard gas or solution containing species A but at a higher concentration than in line 9, $C'_A(o)$, is injected into the dilution flask at time t=o. At time t, when the size of the peak appearing in the plasmagram at point $k_A$ decreases to a level equal to that of the previously recorded calibrant peak, the calibrant gas concentration $C'_A(t)$ can be calculated from Equation (11), above, provided the gas flows through lines 9 and 80 are equal. This concentration naturally is the same as the calibrant A concentration, $\Delta \hat{C}_A$, so that $\Delta \hat{C}_A$ now is known. If the gas flows through lines 9 and 80 are unequal, it is a simple matter to calculate $\Delta \hat{C}_A$ from $C'_A(t)$ using a correction factor. Measurement of $\Delta \hat{C}_A$ should be repeated periodically because of a long-term change of the output of the calibrant source. The carrier gas, respectively, from lines 4 and 2 is now allowed to purge line 9 and the dilution flask 3, while sample gas is admitted to line 1. The gas streams combined in the four-port connector 17 flow to inlet port 18 of plasma chromatograph 10. A plasmagram of the sample gas is recorded (curve D in FIG. 2), and its amplitude at point $k_A$ is determined. The four-way valve 5 is next turned to the dotted-line position to admit to the connector 17 the calibrant gas from the calibrant source 7 through line 9. A plasmagram of this mixture is now recorded (curve E in FIG. 2), and the amplitude $A^*$ of the peak at point $k_A$ is determined. The difference $\Delta \ln A^*]_A$ between the logarithms of the amplitudes at point $k_A$ in curves D and E of FIG. 2 is directly related to the concentration $\hat{C}_A$ of species A in the plasma chromatograph by means of equation 3. When the response is linear to species A, the calibration constant $K_0$ is often small, and sufficient accuracy is obtained by setting $K_0 = 0$ and, by equation (10) identifying $K_1 = 1/\Delta\hat{C}_A$. The expression for the concentration $C_A$ of species A in the sample gas becomes in this case $$C_A = \frac{G\Delta\hat{C}_A}{\ln A^*]_A} \quad (12)$$

For the small relative changes in the peak amplitude or area $A^*$, $\Delta \ln A^*]_A$ can by approximated by $[(\Delta A^*)_A / A^*]$, and equation (12) becomes $$C_A = G\Delta\hat{C}_A \frac{A_c^*}{(\Delta A^*_c)_A} \quad (13)$$

where in equations (12) and (13) $\Delta\hat{C}_A$ is the standardized calibrant concentration value obtained in the earlier calibration step; $A_c^*$ is the corrected peak size of species A on the plasmagram E in FIG. 2 at point $k_A$; $(\Delta A^*_c)_A$ is the amplitude difference at point $k_A$ between plasmagrams E and F in FIG. 2; and G is the ratio of the total gas flow into the plasma chromatograph inlet 18 to the sample gas flow in line 1. The corrected value $A_c^*$ is obtained from the measured value $A^*$ by (1) making a baseline correction on the basis of curve A in FIG. 2 and (2) deconvoluting adjacent peaks. This deconvolution correction can be made by visual observation of graphs or by automatic calculation by computer.

It is to be noted that it is not necessary to measure the gas flows in the course of each analysis. With the use of standard flow control equipment it is possible to maintain constant flows at their preset levels for periods as long as several months or more. Accordingly, it will usually be sufficient to simply occasionally check that the settings of the control equipment and readings of flowmeters are unchanged.

Following the determination of the concentration of species A in a gas sample as described, the same operational sequence can be repeated for additional gas samples. Valve 5 is moved to the position indicated by solid lines, and a new sample is admitted to line 1.

It can be readily seen that it is possible to use the method of the present invention for determining very low concentrations of different chemical species, A, B, C . . . I having characteristic peaks at different points in the plasmagram, $k_A$, $k_B$, $k_C$ . . . $k_I$, corresponding to different drift times. Although each calibrant would have to be standardized, only one exponential dilution flask 3 would be necessary since the flask could be used sequentially to provide calibrant concentrations $C'_A$, $C'_B$, $C'_C$ . . . $C'_I$ in the manner described above. However, a parallel arrangement of a multiplicity of calibration sources 7 would be necessary, and the four-way valve 5 would have to be replaced by an $(I+2)$-way valve.

The above-described procedure will be satisfactory for most cases, at least when the concentration of the species of interest A is small compared to the remaining impurities. In this case the response is substantially linear. In cases, where $\Delta \ln A^*]_A$ is not sufficiently proportional to the concentration of A in the sample, $C_A$, to permit an accurate determination of the concentration of A by means of equations (3), (12), and (13), above, it is recommended that a two-step technique, employing an additional calibrant B, be used. In this case the concentration of A is calculated by means of equation (1), above. Calibrant B should have kinetic properties similar to species A. This usually means that A and B should be chemically similar. In order to avoid overlap of the peak of B with that of A on the plasmagram, species A and B should have different ion mobilities. A desirable calibrant B would be a homologue of A; for example, if A is dimethylnitrosamine, B might be diethylnitrosamine.

In practice, after the first series of operations described above for species A is completed, calibrant B is introduced into the plasma chromatograph through line 9, using a five-way valve instead of the four-way valve 5 shown in FIG. 1. The size of the characteristic peak of B on the plasmagram at its drift time point, $k_B$, is determined (Curve C in FIG. 2); the apparatus is purged with carrier gas; and a known concentration of species B is introduced via the exponential dilution flask 3. Once the concentration of B in calibrant gas stream has been determined, as explained above for calibrant A, the instrument is again purged with the carrier gas. The unknown sample is then introduced and its plasmagram peak characteristic of A at drift time point $k_A$ is measured. A stream of calibrant B is introduced next. The logarithmic change, $\Delta \ln A^*]_B$, of the size of species A's characteristic plasmagram peak at $k_A$ as a result of the presence of calibrant B is determined (Curve F in FIG. 2). These data are used to solve equation (1). The concentration, $C_A$, of species A in the sample is calculated from $\hat{C}_A$ according to equation (2), above. The calibration constants $K_0$, $K_1$ are $K_2$ for equations (1) and (3) are determined for each set of operating conditions using the exponential dilution flask as a source of known concentrations of species A, measuring $\Delta \ln A^*]_A$ and $\Delta \ln A^*]_B$ for different concentrations of A, $(\hat{C}_A)_1$, $(\hat{C}_A)_2$ . . . , and fitting these data to a function of the form of equation (10) by multiple linear regression. Such calculations are well known to a skilled engineer and can also be made routinely by computer.

It would be obvious to one skilled in the art that the above-described sequence of operations, including the opening and closing of various valves and controlling gas flows can be entirely automatic, rather than manual. The four-way valve 5 can be computer-controlled or replaced by separate valves and associated piping, each valve being computer controlled according to an established program. All such automatic or improved alternative ways of carrying out the method of the present invention are within the intended scope of the claims appended hereto.

Furthermore, it is obvious that the above-described sequence of operations is not critical in the sense that, for example, calibrant B may be introduced into the plasma chromatograph before calibrant A, rather than after calibrant A; or that the plasmagram of a mixture of the unknown gas sample with a calibrant may be obtained before the plasmagram of the unknown gas sample alone is obtained.

Finally, it will be recognized that it is not strictly required that plasmagrams of either the unknown gas sample, or calibrants, or mixtures thereof be in fact either displayed or recorded, since the required information on the amplitudes or areas of peaks of interest can be directly obtained from raw data by computer calculation and displayed or recorded in digital form, rather than in graphic form. All such modifications and variations are included within this invention.

While the above-described technique and apparatus have been developed for use in the field of plasma chromatography, it will be recognized that such an operating procedure can be likewise applied to other analytical methods in which a change of amplitude or area of one or more peaks of a spectrum occurs on addition of a calibration standard directly to the sample being measured.

PREFERRED EMBODIMENT

Figure 3:
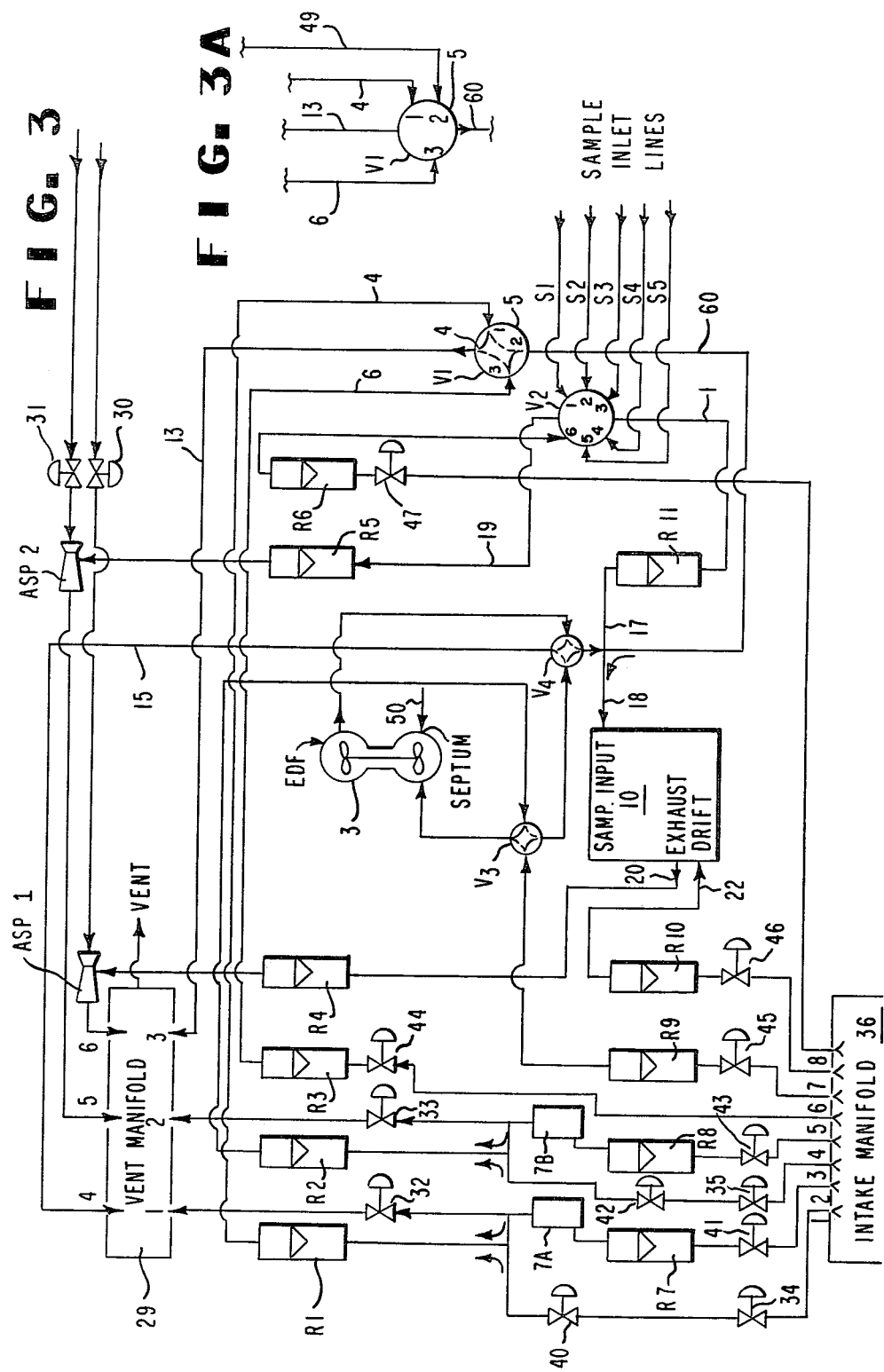
FIG. 3 is a schematic flow diagram of the preferred embodiment of the calibration system.

FIG. 3 is a schematic diagram of what is presently considered to be the preferred embodiment of a plasma chromatograph calibration system according to the present invention. Plasma chromatograph 10 has sample inlet port 18, a drift gas port 22, and an exhaust port 20. Sample lines $S_1$, $S_2$, $S_3$, $S_4$, and $S_5$ communicate through valve V2 with sample line 1 and, via connector 17, with plasma chromatograph 10. Valve V2 also is connected through line 19 to the vent manifold 29. Valve 5 (V1) admits to the plasma chromatograph either carrier gas from line 6 or calibrant A from calibrant source 7A plus carrier from line 4. This valve also communicates with the vent via line 13. Valves V3 and V4 are normally operated in unison, that is, they are set so that gases either flow through both valves according to the solid paths or flow through both valves according to the dotted paths. When the solid paths are followed, carrier gas flows to the plasma chromatograph, and calibrant A from source 7B flows through the exponential dilution flask 3, then, via line 15, to the vent manifold 29. When the dotted paths are followed, calibrant A in the exponential dilution flask 3 is diluted with carrier gas from rotameter R9 and purged into the plasma chromatograph 10, while the stream of calibrant from source 7B is vented through line 15.

In this preferred embodiment calibrant B is not used. When, however, it is desired to also use calibrant B, the apparatus is slightly modified, as shown in FIG. 3A, which shows a different type of valve V1. This valve is connected, as before, to the vent through line 13, to valve V4 through line 60, to the intake manifold through line 6, and to the calibrant A source through line 4. In addition, this valve V1 is connected through line 49 to the calibrant B source (not shown). For this modification, valve V1 has five ports instead of four. When calibrant B is used, it is introduced into the exponential dilution flask 3 with a liquid or gas syringe through the septum port 50. Nitrogen for all instrument needs is supplied from the intake manifold 36, while all the exhaust streams are directed to the vent manifold 29. Rotameters R1 through R11 are used to measure gas flows in all the lines. Other means for measuring the gas flows, such as electronic mass flow transducers, could also be used. Gas flows are controlled by means of metering valves 30–35 and flow control valves 40–47. ASP1 and ASP2 are, respectively, plasma chromatograph and sample exhaust aspirators.

While the calibrant source illustrated in FIG. 1 is a permeation tube, other calibrant sources, such as, for example, permeation wafers and diffusion tubes, can be used equally well. A good discussion of devices for preparing low-level gas mixtures by A. J. Martin, F. J. Debbrecht, and G. R. Umbreit has been published by Analytical Instrument Development, Inc., Route 41 and Newark Road, Avondale, Pa. 19311.

In the preferred mode of operation of the calibration system shown in FIGS. 3 and 3A a continuous, constant flow of gas from the four-port connector 17 to the inlet port 18 of the plasma chromatograph 10 is insured for all valve settings according to the following Table 1:

TABLE 1

| OPERATION | V1 | V2 | V3 | V4 |
|---|---|---|---|---|
| A. Carrier Gas Purge of Plasma Chromatograph; Charging Dilution Flask With Calibrant A | Solid Paths | Position 6 to Line 1; Inputs 1–5 to Line 19 | Solid Paths | Solid Paths |
| B. Standardization of Calibrant A (via dilution flask) + Carrier | Solid Paths | Position 6 to Line 1; Inputs 1–5 to Line 19 | Dotted Paths | Dotted Paths |
| C. Sample 1 + Carrier | Solid Paths | Input 1 to Line 1; Inputs 2–6 to Line 19 | Solid Paths | Solid Paths |
| D. Sample 1 + Calibrant A + Carrier | Dotted Paths | Input 1 to Line 1; Inputs 2–6 to Line 19 | Solid Paths | Solid Paths |

When calibrant B is also used the sequence of operations, and the valve settings are shown in Table 2, below:

TABLE 2

| OPERATION | V1 | V2 | V3 | V4 |
|---|---|---|---|---|
| A. Carrier Gas Purge of Plasma Chromatograph; Charging Dilution Flask With Calibrant A | Input 3 to Line 60; Inputs 1, 2 to Line 13 | Input 6 to Line 1; Inputs 1–5 to Line 19 | Solid Paths | Solid Paths |
| B. Standardization of Calibrant A (via Dilution Flask) + Carrier | Input 3 to Line 60; Inputs 1, 2 to Line 13 | Input 6 to Line 1; Inputs 1–5 to Line 19 | Dotted Paths | Dotted Paths |
| C. Standardization of Calibrant B (via Dilution Flask) + Carrier* | Input 3 to Line 60; Inputs 1, 2 to Line 13 | Input 6 to Line 1; Inputs 1–5 to Line 19 | Dotted Paths | Dotted Paths |
| D. Sample 1 + Carrier | Input 3 to Line 60; Input 1, 2 to Line 13 | Input 1 to Line 1; Inputs 2–6 to Line 19 | Solid Paths | Solid Paths |
| E. Sample 1 + Calibrant A + Carrier | Input 1 to Line 60; Inputs 2, 3 to Line 13 | Input 1 to Line 1; Inputs 2–6 to Line 19 | Solid Paths | Solid Paths |
| F. Sample 1 + Calibrant B + Carrier | Input 2 to Line 60; Inputs 1, 3 | Input 1 to Line 1; Inputs 2–6 | Solid Paths | Solid Paths |

TABLE 2-continued

| OPERATION | V1 | V2 | V3 | V4 |
|---|---|---|---|---|
| | to Line 13 | to Line 19 | | |

*Dilution flask to be charged with calibrant B through Septum 50.

Valves, fittings, and other associated equipment are standard parts obtainable from regular suppliers. Valve V1 shown in FIGS. 1 and 3 can be, for example, valve ASC-4-HPa, and valve V2 can be valve ASC-6-HPa, both manufactured by Valco Instrument Co., Houston, Tex. Valve V1 shown in FIG. 3A is identical to valve V2, except that it has fewer inlet ports. Valves V3 and V4 are, for example 2X inert valves, part No. 86405, of Hamilton Co. of Reno, Nev. Aspirators ASP1 and ASP2 typically are vacuum flow transducers type AVRH-093, manufactured by Air-Vac Engineering Co. of Milford, Conn., and are serviced by high pressure air (typically, $5.5 \times 10^5$ Pa). The metering valves 30 and 31 typically are NuPro type SS-4MA, manufactured by NuPro Company, Cleveland, Ohio. Permeation tubes 7A and 7B can be purchased as complete oven arrangements from the manufacturer, Kin-Tek Laboratories, Texas City, Tex., catalog No. 71014. Metering valves 32 and 33 are NuPro type SS-2SA.

The eight-port nitrogen intake manifold 36 (typically, a modified NuPro type SS-4CS-TSW-50) distributes the nitrogen supply at about $1.4 \times 10^5$ Pa to the outlet ports, the flow from each port being set and regulated by means of metering valves and flow control valves. Metering valves 34 and 35 are NuPro SS-2SA. Flow control valves 40 and 46 are type 8944 #4SS made by Brooks Instrument Division of Emerson Electric Company, Hatfield, Pa., while flow control valves 41-45 and 47 are type E2P-G114ELF manufactured by Air Products and Chemical Co., Tamaqua, Pa. Rotameters R1-R3 and R7-R10 are steel ball Sho-Rate type R-2-15-AAA, and rotameters R4-R6 and R11 are glass ball Sho-Rate type R-2-15-A made by Brooks Instrument Division of Emerson Electric Company, Hatfield, Pa. The exponential dilution flask 3 is made by Glenco Scientific, Inc. of Houston, Tex. The flask can be adapted for either remote sample injection or direct syringe injection of the calibrant.

EXAMPLE 1

Using the equipment and flow system illustrated in FIG. 3, the concentration of hexafluoroacetone in air was determined according to the procedure of Table 1, above, as follows. The exponential dilution flask was maintained at 100° C. All gas flows into connector 17, except in Step D, were maintained at 50 cc/min. Plasmagrams of ion current vs. ion drift time were obtained with a Nicolet 1170 signal averager and a model 171/2 signal digitizer. Signal amplitudes at channels k=344 and 387 on the horizontal axis of the plasmagrams were recorded. The channel number is directly proportional to ion drift time and inversely proportional to ion mobility. The plasmagrams 4A, 4B, and 4C in FIG. 4 cover drift times between 0 and 20 msec.

Curve A in FIG. 4 is the plasmagram of the unknown air sample alone. Curve B in FIG. 4 is the plasmagram of an air sample to which a quality $\Delta \hat{C}_A$ equal to 0.016 ppm of hexafluoroacetone was added (according to step D of Table 1 above). Curve C is the graph of the difference between plasmagrams A and B of FIG. 4. For better reading accuracy, this graph is enlarged twice.

The corrected plasmagram peak amplitude of hexafluoroacetone, $A_c^*$, was obtained by subtracting from the plasmagram A in FIG. 4, at channel 387 the baseline determined for a nitrogen blank (obtained in step A). Since no attempt was made to deconvolute the adjacent peaks, this corrected peak amplitude represents the upper limit of hexafluoroacetone concentration in the air sample, which was calculated from equation (13), after the following values had been determined:

$$G = 1.6;\ \Delta \hat{C}_A = 0.016\ \text{ppm; and}\ \frac{A^*_c}{\Delta A^*_c} = 0.31.$$

The upper limit of hexafluoroacetone concentration is 8 ppb.

EXAMPLE 2

FIG. 5 compares the results according to this invention in the determination of dimethylnitrosamine in air with those obtained without calibration. A constant stream of air containing about 0.5 ppb of dimethylnitrosamine was introduced into the sampling port of a plasma chromatograph. Various gaseous or volatile chemical compounds, which served as "background contaminants", were introduced sequentially through a parallel input via the exponential dilution flask at concentrations which changed continuously with time. Those compounds were as follows: (1) dimethylamine, (2) a mixture of ethyl benzoate, ethylenediamine, and bis(2-methoxyethylethyl), and (3) 1,2-dimethoxyethane. Curve A shows the amplitude variation of the dimethylnitrosamine peak A* on the plasmagram as a function of elapsed time. Curve B was obtained according to the method of this invention, using dimethylnitrosamine as the calibrant standard A. For better reading accuracy, the A*/ΔA* value has been multiplied by 100.

It can be seen that the amplitude of peak A* varied over a broad range as a result of the addition of the "background contaminants", even though the concentration of dimethylnitrosamine was kept constant. The points of addition of the above "contaminants" (1), (2), and (3) are marked in FIG. 5 by vertical arrows along the abscissa. It is noted that the greatest variations of A* occurred immediately after each addition. However, the ratio A*/ΔA* varied during the same period much more narrowly, and those variations occurred at random, rather than at the time of, or following, addition of another compound. A comparison of curves A and B shows the scatter of A* values to be approximate 9–10 times larger than the scatter of A*/ΔA*.

We claim:

1. A method for determining a concentration, $C_A$, of an ionizable species A in a gas sample by plasma chromatography, comprising the following steps:
   (a) introducing into the plasma chromatograph a gas sample containing an unknown concentration of species A, and determining the size, A* (amplitude or area), of the characteristic peak of an ion formed by species A in the plasma chromatograph at its characteristic point $k_A$ on a plasmagram correlating ion mobility or drift time with ion current intensity;
   (b) while maintaining the flow of the gas sample into the plasma chromatograph, introducing into the plasma chromatograph an inert carrier gas containing a discrete amount $\Delta C_A$ of species A, such that the concentration of species A in the plasma chromatograph is increased by the amount $\Delta \hat{C}_A$, and determining the resulting logarithmic change, $\Delta \ln A^*]_A$, in the size of the characteristic ion peak of species A at point $k_A$ in the plasmagram;

(c) while maintaining the flow of the gas sample into the plasma chromatograph, but cutting off the flow of carrier gas containing species A, introducing into the plasma chromatograph an inert carrier gas containing a discrete amount $\Delta C_B$ of species B having kinetic characteristics similar to those of species A but forming an ion whose mobility is different from that of the ion formed from A, the change in concentration of species B in the plasma chromatograph being $\Delta \hat{C}_B$, and determining the resulting logarithmic change of the size (amplitude or area) $\Delta \ln A^*]_B$ of the characteristic ion peak of species A at point $k_A$ in the plasmagram;

purging the plasma chromatograph with the carrier gas before one or more of the above steps (a) through (c) and maintaining during the entire operation through step (c) known flows of the gas sample and of the carrier gas, either alone or containing either species A or species B;

(d) calculating the concentrations $\hat{C}_A$ of species A in the plasma chromatograph from the following equation (1):

$$\frac{1}{\hat{C}_A} = K_0 + K_1\{\Delta \ln A^*]_A\} + K_2\{\Delta \ln A^*]_B\} \quad (1)$$

where $A^*$ is the size of the plasmagram peak of the characteristic ion formed by A; $\Delta \ln A^*]_A$ denotes the change in $\ln A^*$ on addition of $\Delta C_A$; $\Delta \ln A^*]_B$ denotes the change in $\ln A^*$ on addition of $\Delta C_B$; and $K_0$, $K_1$, and $K_2$ are calibration constants; and calculating the concentration, $C_A$, of species A in the gas sample by means of the following equation (2)

$$C_A = G \cdot \hat{C}_A \quad (2)$$

wherein G is the ratio of the total gas flow through the plasma chromatograph in step (a), above, to the flow of the gas sample through the sample introduction means;

with the provision that when the concentrations $\hat{C}_A$ and $(\hat{C}_A + \Delta \hat{C}_A)$ are sufficiently smaller than the sum $$\sum_i \hat{C}_i$$

of all other ionizable species concentrations in the plasma chromatograph, so that $\Delta \ln A^*]_A$ is proportional to $\Delta \hat{C}_A$, the above step (c) can be omitted, and the concentration $\hat{C}_A$, of species A in the plasma chromatograph can be calculated from the following equation (3)

$$\frac{1}{\hat{C}_A} = K_0 + K_1\{\Delta \ln A^*]_A\} \quad (3)$$

wherein $K_0$ and $K_1$ have the same meaning as in the above equation (1).

2. The method of claim 1 wherein only one species of known, discrete concentration is used, this species being the same as species A in the unknown sample.

3. The method of claim 1 wherein two species of known, discrete concentrations, one of which is the same as species A in the unknown sample, are used sequentially.

4. The method of claim 1 wherein concentrations of a plurality of ionizable species in a gas sample are determined sequentially, a known discrete amount of an ionizable species, the same as each individual species in the unknown sample, being used as a calibrant in conjunction with the determination of the concentration of each such species.

5. The method of claim 1 wherein the carrier gas is nitrogen.

6. Apparatus for the determination of a concentration, $C_A$, of an ionizable species A in a gas sample by plasma chromatography, said apparatus comprising:

(A) a plasma chromatograph drift tube having a gas inlet, a gas outlet, an ion source close to the gas inlet, a shutter grid, and an ion collector, said collector being connected to a means for measuring ion current flowing through the drift tube;

(B) a means for introducing into said drift tube a gas sample containing an unknown concentration of species A;

(C) a means for introducing into said drift tube known, discrete amounts of one or more calibrant species in a carrier gas, both in the absence and in the presence of the gas sample containing an unknown concentration of species A;

(D) a means for accurately standardizing the concentration of the calibrant species in the carrier gas;

(E) a means for introducing into the drift tube the carrier gas alone;

(F) a means for maintaining controlled flows of all gases entering the drift tube;

(G) a means for purging the drift tube with carrier gas alone between ion current measurements, and a means for introducing into the drift tube one or more of any desired calibrant species and unknown gas samples in any order;

(H) a means for obtaining and recording data correlating the plasma chromatograph ion current with the ion mobility or drift time of ions formed by the species of interest and by calibrant species.

7. Apparatus of claim 6 wherein a known concentration of a calibrant species in the carrier gas is delivered from a permeation tube contained in a thermostatted vessel.

8. Apparatus of claim 6, wherein the concentration of a calibrant species in the carrier gas is standardized by means of an exponential dilution flask being connected in parallel with the source of the calibrant species in such a manner that the outflow from the exponential dilution flask and from the calibrant species source can be introduced into the plasma chromatograph sequentially.

* * * * *